(12) United States Patent
Woodcraft et al.

US008946410B2

(10) Patent No.: US 8,946,410 B2
(45) Date of Patent: Feb. 3, 2015

(54) AUTOMATED RADIOSYNTHESIS

(75) Inventors: John Woodcraft, Amersham (GB); L Clare Jones, Amersham (GB); Alessandra Gaeta, Amersham (GB); John William Trigg, Amersham (GB); Alexander Paul Jones, Amersham (GB); Stuart Plant, Amersham (GB); Alexander Jackson, Amersham (GB)

(73) Assignee: GE Healthcare Limited, Amersham, Buckinghamshire (GB)

( * ) Notice: Subject to any disclaimer, the term of this patent is extended or adjusted under 35 U.S.C. 154(b) by 0 days.

(21) Appl. No.: 13/394,655

(22) PCT Filed: Oct. 8, 2010

(86) PCT No.: PCT/EP2010/065077
§ 371 (c)(1),
(2), (4) Date: Apr. 10, 2012

(87) PCT Pub. No.: WO2011/042529
PCT Pub. Date: Apr. 14, 2011

(65) Prior Publication Data
US 2012/0190843 A1  Jul. 26, 2012

Related U.S. Application Data

(60) Provisional application No. 61/250,892, filed on Oct. 13, 2009.

(30) Foreign Application Priority Data

Oct. 8, 2009 (GB) .................................. 0917611.6

(51) Int. Cl.
*C07D 487/04* (2006.01)
(52) U.S. Cl.
CPC .................................. *C07D 487/04* (2013.01)
USPC ....................................................... 540/498
(58) Field of Classification Search
CPC .................................................... C07D 487/04
See application file for complete search history.

(56) References Cited

U.S. PATENT DOCUMENTS 4,352,815 A * 10/1982 Hunkeler et al. ........ 514/210.16

FOREIGN PATENT DOCUMENTS

| EP | 0433163 | | 3/2012 |
| WO | WO 97/34898 | * | 9/1997 |
| WO | 2005/097713 | | 10/2012 |

OTHER PUBLICATIONS

Miller, P.W., et al. "Synthesis of 11C, 18F, 15O, and 13N Radiolabels for Positron Emission Tomography." Angew. Chem. Int. Ed. (2008), vol. 47, pp. 8998-9033.*
Hand, K.S.P., et al. "Central benzodiazepine receptor autoradiography in hippocampal sclerosis." British Journal of Pharmacology. (1997), vol. 122, pp. 358-364.*
Miller, Angewandte Chemi, vol. 47, No. 47, 2008 pp. 8998-9003.
Ryzhikov, Nuclear Medicine and Biology, vol. 32, No. 2, 2005 pp. 109-116.
Massaweh, Nuclear Medicine and Biology, vol. 36 No. 7, 2009, pp. 721-727.
Mandap, Nuclear Medicine and Biology vol. 36, 2009 pp. 403-409.
Ryzhikov, Radiochemistry, Vol. 46, No. 3, 2004 pp. 290-294.
GB0917611.6 Search Report Dated Feb. 9, 2010.
PCT/EP2010/065077 ISRWO Dated Jan. 20, 2011.
Westera, et al. European Journal of Nuclear Medicine, vol. 23, No. 1, Jan. 1996.
Moerlein, et al. European Journal of Pharmacology, vol. 218, 1992, pp. 109-115.
Teng, et al. Nuclear Medicine and Biology, vol. 17, No. 8, 1990 pp. 811-817.
Mitterhauser, et al. Nuclear Medicine and Biology vol. 31, 2004, pp. 291-295.
Moerlein, et al. Symposium Abstracts Paged 316-318, (c) Jan. 1993.
Halldin, et al. Applied Radiation Iosotopes, vol. 39, No. 9, 1988 pp. 993-997.

* cited by examiner

*Primary Examiner* — Andrew D Kosar
*Assistant Examiner* — John S Kenyon

(57) ABSTRACT

The present invention provides a method to obtain radiofluorinated compounds useful for in vivo imaging $GABA_A$ receptors. The method of the invention is high-yielding and may conveniently be carried out on an automated synthesizer such as Fastlab™. A further aspect of the invention is a cassette suitable for carrying out the automated method of synthesis of the invention. Novel precursor compounds useful in the method of the invention are also provided, as are a number of novel compounds obtained by the method of the invention.

11 Claims, No Drawings

AUTOMATED RADIOSYNTHESIS

This application is a filing under 35 U.S.C. 371 of international application number PCT/EP2010/065077, filed Oct. 8, 2010, which claims priority to U.S. application No. 61/250,892 filed Oct. 13, 2009 and Great Britain application number 0917611.6 filed Oct. 8, 2009, the entire disclosure of each of which is hereby incorporated by reference.

TECHNICAL FIELD OF THE INVENTION

The present invention relates to in vivo imaging and in particular to in vivo imaging of gamma-aminobutyric acid (GABA) receptors of the central nervous system (CNS). The invention provides a method suitable for the automated synthesis of radiofluorinated GABA receptor antagonist compounds.

DESCRIPTION OF RELATED ART

Gamma-aminobutyric acid (GABA) is the most important inhibitory neurotransmitter in the human brain. GABA receptors are transmembrane receptors and fall into two main types, $GABA_A$ receptors and $GABA_B$ receptors. $GABA_A$ receptors have been the major focus of pharmacological development to date. Many $GABA_A$ receptor subtypes have been discovered and novel chemical structures have been developed which are selective for these subtypes. Normal activation of the $GABA_A$ receptor results in chloride ion being selectively conducted through its pore. This chloride channel gating is generally inhibitory on a neuron by virtue of stabilising the membrane potential near to resting level.

Defective $GABA_A$ receptor neurotransmission may be caused by a reduction in $GABA_A$ receptors, or by defective functioning of the $GABA_A$ receptor due to e.g. a genetic mutation in a $GABA_A$ receptor gene, traumatic brain injury, or a pharmacological insult, and is implicated in a number of neurological and psychiatric disorders, including epilepsy, anxiety disorders, Parkinson's disease and chronic pain. The development of radioligands selective for the $GABA_A$ receptor is therefore of value in terms of brain imaging studies in living human patients, in particular those suffering from disorders associated with defective $GABA_A$ receptor neurotransmission.

Flumazenil (also known as flumazepil, code name Ro 15-1788, trade names Anexate, Lanexat, Mazicon, Romazicon) is an imidazo[1,5-a][1,4]benzodiazepine that is a neutralising allosteric modulator of $GABA_A$ receptors in the CNS (Johnston 1996 Pharmacol Ther; 69(3): 173-198). The most common use of flumazenil to date has been as an antidote to benzodiazepine overdose as it reverses the effects of benzodiazepines by competitive inhibition at the benzodiazepine binding site of the $GABA_A$ receptor. In addition, because flumazenil has little or no agonist activity, radiolabelled versions thereof have been developed as positron emission tomography (PET) radiotracers.

[$^{18}$F]FMZ has the same chemical formula as flumazenil but wherein $^{18}$F is incorporated by direct radiofluorination of a nitro precursor:

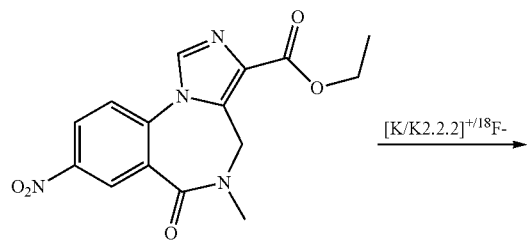

[K/K2.2.2]$^{+/18}$F-

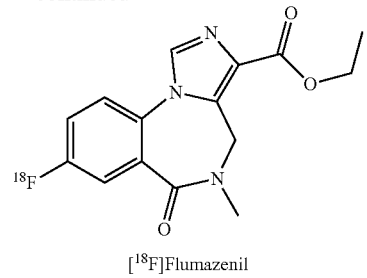

[$^{18}$F]Flumazenil

[$^{18}$F]FMZ binds to the $GABA_A$ receptor with high affinity ($K_i$ around 0.5 nM) and selectivity. Ryzhikov et al (2005 Nuc Med Biol; 32: 109-116) describe the preparation of [$^{18}$F]FMZ from a nitro precursor compound. This synthesis, however, has been found by the present inventors to have a less than optimal end of synthesis (EOS) yield of 2.7-7.7% (described herein as a comparative example). These EOS yields are comparable to those reported by Odano et al (Neuroimage 2009; 45(3): 891-902).

The present invention seeks means to obtain radiofluorinated agents that bind to the $GABA_A$ receptor with high affinity in improved yields compared to the prior art methods.

SUMMARY OF THE INVENTION

The present invention provides a method to obtain radiofluorinated compounds useful for in vivo imaging $GABA_A$ receptors. The method of the invention is high-yielding in comparison to the prior art methods. A further aspect of the invention is a cassette suitable for carrying out the automated method of synthesis of the invention. Novel precursor compounds useful in the method of the invention are also provided, as are certain novel radiofluorinated compounds obtained by the method of the invention.

DETAILED DESCRIPTION OF THE INVENTION

In one aspect, the present invention provides a method to obtain a compound of Formula I:

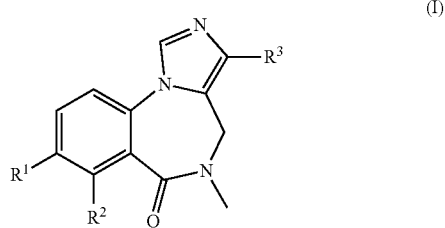

wherein:
one of $R^1$ and $R^2$ is $^{18}$F and the other is hydrogen; and,
$R^3$ is a $C_{3-5}$ heterocycle; or, $R^3$ is C(=O)—O—$R^4$ wherein $R^4$ is hydrogen, or a straight- or branched-chain $C_{1-4}$ alkyl;
wherein said method comprises:
(i) providing a precursor compound of Formula Ia:

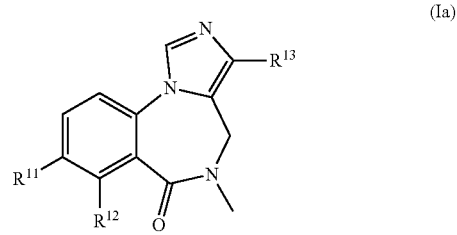

wherein:

one of $R^{11}$ and $R^{12}$ is a leaving group and the other is hydrogen, wherein:

when $R^{11}$ is said leaving group it is selected from tri-$C_{1-3}$ alkyl ammonium or —$I^+$—Ar, wherein Ar is phenyl substituted with one or more R* groups, wherein R* is selected from hydrogen, nitro, cyano, halogen, $C_{1-10}$ hydroxyalkyl, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{2-10}$ alkenyl, and $C_{2-10}$ alkynyl; and, when $R^{12}$ is said leaving group it is selected from nitro, tri-$C_{1-3}$ alkyl ammonium or —$I^+$—Ar, wherein Ar is as defined above for $R^{11}$; and, $R^{13}$ is as defined for $R^3$ of Formula I; and, (ii) reacting said precursor compound with a suitable source of [$^{18}$F]Fluoride.

A "precursor compound" comprises a non-radioactive derivative of a radiolabelled compound, designed so that chemical reaction with a convenient chemical form of the detectable label occurs site-specifically; can be conducted in the minimum number of steps (ideally a single step); and without the need for significant purification (ideally no further purification), to give the desired in vivo imaging agent. Such precursor compounds are synthetic and can conveniently be obtained in good chemical purity. The precursor compound may optionally comprise a protecting group for certain functional groups of the precursor compound.

A "leaving group" is a substituent of the precursor compound as defined above which is replaced with $^{18}$F when the precursor compound is reacted with a suitable source of [$^{18}$F] fluoride, thereby permitting incorporation of $^{18}$F site-specifically to result in the desired radiofluorinated compound of Formula I.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as tetrabutyldimethylsilyl. The use of further protecting groups are described in 'Protective Groups in Organic Synthesis', Theorodora W. Greene and Peter G. M. Wuts, (Third Edition, John Wiley & Sons, 1999).

The term "alkyl" used either alone or as part of another group is defined herein as any straight, branched or cyclic, saturated or unsaturated $C_nH_{2n+1}$ group.

The term "aryl" used either alone or as part of another group is defined herein as any $C_{6-14}$ molecular fragment or group which is derived from a monocyclic or polycyclic aromatic hydrocarbon, or a monocyclic or polycyclic heteroaromatic hydrocarbon.

The term "halogen" means a group selected from fluorine, chlorine, bromine, and iodine.

The term "nitro" refers to the group —$NO_2$.

The term "cyano" refers to the group —CN.

The term "carboxyalkyl" refers to an alkyl group as defined above substituted with at least one —COOH.

The term "alkoxyalkyl" refers to an alkyl ether radical wherein the term alkyl is as defined above.

The term "hydroxyalkyl" refers to an alkyl radical as defined above wherein at least one hydrogen atom has been replaced by an —OH group.

The term "aminoalkyl" refers to an alkyl radical as defined above wherein at least one hydrogen atom has been replaced by an —$NH_2$ group.

The term "haloalkyl" refers to an alkyl radical as defined above wherein at least one hydrogen atom has been replaced by a halogen wherein halogen is as defined herein.

The term "heteroaryl" refers to an aryl as defined above wherein at least one carbon atom is replaced with a heteroatom selected from O, N and S.

The term "alkylaryl" refers to an alkyl radical as defined above in which at least one hydrogen atom is replaced by an aryl radical as defined above.

The term "heterocycle" refers herein to an aliphatic or aromatic cyclic radical wherein the cycle comprises one or more heteroatoms selected from nitrogen, oxygen or sulfur.

The term "alkenyl" means a straight-chain or branched-chain hydrocarbon radical having one or more double bonds.

The term "alkynyl" means a straight-chain or branched chain hydrocarbon radical having one or more triple bonds.

In a preferred embodiment of the method of the invention where $R^1$ is $^{18}$F, $R^{11}$ is trimethyl ammonium or —$I^+$—Ar.

In a most preferred embodiment of the method of the invention $R^2$ is $^{18}$F. When $R^2$ is $^{18}$F, it is preferred that $R^{12}$ is nitro, trimethyl ammonium or —$I^+$—Ar. When $R^2$ is $^{18}$F, it is most preferred that $R^{12}$ is nitro.

$R^3$ of Formula I and $R^{13}$ of Formula Ia are the same and are preferably C(=O)—O—$R^4$, wherein $R^4$ is straight or branched-chain $C_{1-14}$ alkyl, preferably methyl, ethyl, isopropyl or tert-butyl. $R^4$ is most preferably ethyl, isopropyl or tert-butyl, and especially preferably ethyl.

The reaction scheme disclosed by Yang et al (2009 Synthesis; 6: 1036-1040) can be adapted to obtain precursor compounds of Formula Ia wherein $R^{11}$ is a leaving group. Scheme 1 illustrates how the precursor compounds can be obtained:

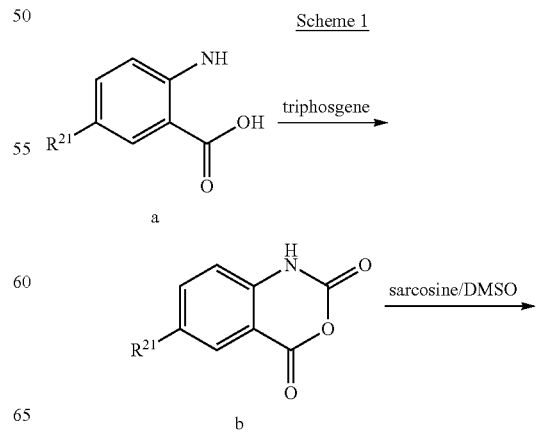

Scheme 1

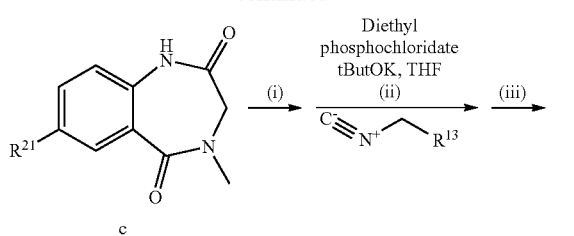

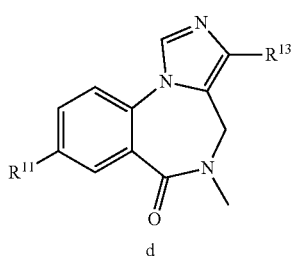

In Scheme 1, where $R^{11}$ is trialkylammonium, $R^{21}$ is $NO_2$, and where $R^{11}$ is an iodonium salt, $R^{21}$ is bromine. $R^{13}$ is as defined for Formula Ia. The appropriate amino benzoic acid compound a, equipped to perform the required chemistry to introduce the desired leaving group at later stage, is reacted with triphosgene to afford the benzoxazine-2,4-dione intermediate b. Reaction of b with sarcosine in DMSO yields the benzodiazepine c. At this stage, where $R^{11}$ is trialkylammonium, $R^{21}$ of compound c is converted to trialkylammonium in step (i) before carrying out step (ii) to obtain compound d. Where $R^{11}$ is an iodonoim salt, $R^{21}$ is converted to the iodonium salt in step (iii) after carrying out step (ii).

Where $R^{12}$ is the leaving group, Scheme 2 may be used to obtain the precursor compound:

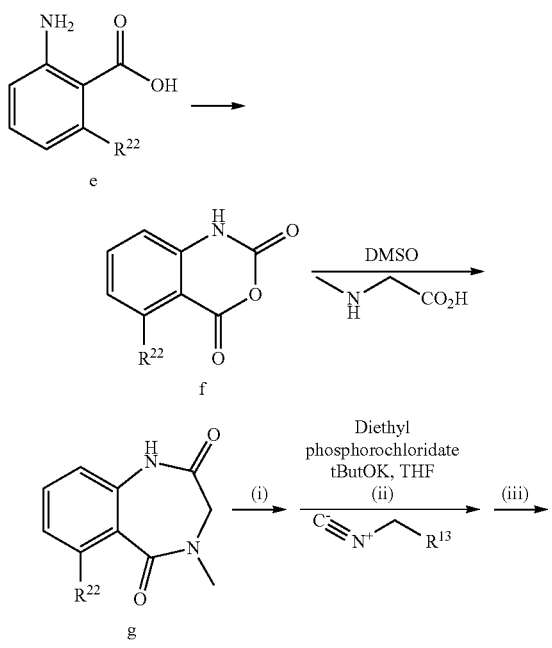

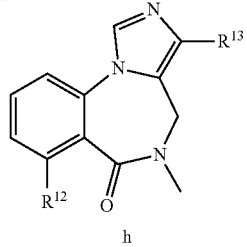

$R^{22}$ is as defined for $R^{21}$ in Scheme 1 above. Compound e is obtained from commercially-available 2,6-dinitro benzoic acid starting material by standard chemical transformations. Compound e is treated as described for compound a of Scheme 1 to give the benzodiazepine intermediate g, which in turn is transformed in the desired imidazobenzodiazepine either before (i.e. (ii) and then (iii)) or after (i.e. (i) and then (ii)) introducing the desired leaving group. Steps (i)-(iii) are as described above in relation to Scheme 1.

[$^{18}$F]Fluoride is typically obtained as an aqueous solution which is a product of the irradiation of an [$^{18}$O]-water target. It has been widespread practice to carry out various steps in order to convert [$^{18}$F]Fluoride into a reactive nucleophilic reagent, such that it is suitable for use in nucleophilic radio-labelling reactions. These steps include the elimination of water from [$^{18}$F]-fluoride ion and the provision of a suitable counterion (*Handbook of Radiopharmaceuticals* 2003 Welch & Redvanly eds. ch. 6 pp 195-227). Nucleophilic radiofluorination reactions are then carried out using anhydrous solvents (Aigbirhio et al 1995 J Fluor Chem; 70: 279-87). In order to increase the reactivity of fluoride and to avoid hydroxylated by-products resulting from the presence of water, water is typically removed from [$^{18}$F]Fluoride prior to the reaction and the radiofluorination reactions are carried out using anhydrous reaction solvents (Aigbirhio et al 1995 J Fluor Chem; 70: 279-87). The removal of water from the [$^{18}$F]Fluoride is referred to as making "naked" [$^{18}$F]Fluoride. This is regarded in the prior art relating to nucleophilic fluoridation as a step necessary to increase the reactivity of fluoride as well as to avoid hydroxylated by-products resulting from the presence of water (Moughamir et al 1998 Tett Letts; 39: 7305-6).

A further step that is used to improve the reactivity of [$^{18}$F]Fluoride for radiofluoridation reactions is to add a cationic counterion prior to the removal of water. The counterion should possess sufficient solubility within the anhydrous reaction solvent to maintain the solubility of the fluoride ion. Counterions that have been used include large but soft metal ions such as rubidium or caesium, potassium complexed with a cryptand such as 4,7,13,16,21,24-Hexaoxa-1,10-diazabicyclo[8.8.8]hexacosane (KRYPTOFIX 222™), or tetraalkylammonium salts. A preferred suitable source of [$^{18}$F]Fluoride for use in the method of the invention is selected from [$^{18}$F] potassium fluoride and [$^{18}$F] caesium fluoride. [$^{18}$F] potassium fluoride is most preferred, and especially preferably when it is complexed with a cryptand such as 4,7,13,16,21,24-Hexaoxa-1,10-diazabicyclo[8.8.8]hexacosane (KRYPTOFIX 222™) because of its good solubility in anhydrous solvents and enhanced fluoride reactivity.

In a preferred embodiment, the method of the invention may further comprise:
(iii) removal of excess [$^{18}$F]Fluoride; and/or,
(iv) removal of any protecting groups; and/or,
(v) removal of organic solvent; and/or, (vi) formulation of the resultant compound together with a biocompatible carrier to obtain a radiopharmaceutical composition suitable for mammalian administration.

The "biocompatible carrier" is a fluid, especially a liquid, in which the radiofluorinated compound is suspended or dissolved, such that the radiopharmaceutical composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like). The biocompatible carrier may also comprise biocompatible organic solvents such as ethanol. Such organic solvents are useful to solubilise more lipophilic compounds or formulations. Preferably the biocompatible carrier is pyrogen-free water for injection, isotonic saline or an aqueous ethanol solution. The pH of the biocompatible carrier for intravenous injection is suitably in the range 4.0 to 10.5.

Currently, the synthesis of $^{18}$F-labelled compounds, particularly for use as PET tracers, is most conveniently carried out by means of an automated synthesis apparatus, e.g. Tracerlab™ and Fastlab™ (both GE Healthcare). However, the prior art method is not suitable for automation. In Comparative Example 1 herein it is demonstrated that radiofluorination of nitromazenil is not an ideal approach for the automated synthesis of [$^{18}$F]FMZ on Fastlab due to the low yield, and also because of the temperature required to obtain effective incorporation of [$^{18}$F]fluoride. The existing FASTlab reaction vessel is made of a cyclo-olefin co-polymer (COC) which can be used at temperatures up to 130° C. The prior art method used to prepare [$^{18}$F]FMZ from a nitro precursor requires a temperatures of around 160° C. At these temperatures the COC reaction vessel loses containment.

As demonstrated in the experimental examples below, changing the leaving group on the nitromazenil precursor from nitro to trimethylammonium allowed the reaction temperature to be reduced to 130° C. whilst maintaining an EOS yield of 7%. Moving the nitro leaving group from the position meta to the amide carbonyl to the position ortho to the amide carbonyl gave an improvement in EOS yield from 2.7-7.7% to 18-23% whilst also reducing the reaction temperature.

In a particularly preferred embodiment, the method of the invention is automated. The radiochemistry is performed on the automated synthesis apparatus by fitting a "cassette" to the apparatus. Such a cassette normally includes fluid pathways, a reaction vessel, and ports for receiving reagent vials as well as any solid-phase extraction cartridges used in post-radiosynthetic clean up steps.

In a further aspect of the present invention there is provided a cassette for carrying out the automated method of the invention comprising:

(i) a vessel containing a precursor compound, wherein said precursor compound is as suitably and preferably defined above; and (ii) means for eluting the vessel with a suitable source of [$^{18}$F]Fluoride, wherein said suitable source of [$^{18}$F]Fluoride is as suitably and preferably defined above.

The cassette may also comprise an ion-exchange cartridge for removal of excess $^{18}$F. The reagents, solvents and other consumables required for the automated synthesis may also be included together with a data medium, such as a compact disc carrying software, which allows the automated synthesiser to be operated in a way to meet the end user's requirements for concentration, volumes, time of delivery etc.

In another aspect, the present invention provides a compound of Formula I as defined in the method of the invention wherein $R^1$ is hydrogen, $R^2$ is [$^{18}$F], and $R^4$ is ethyl, isopropyl or t-butyl, wherein $R^4$ is most preferably ethyl.

In a yet further aspect, the present invention provides a precursor compound of Formula Ia is as defined above wherein one of $R^{11}$ and $R^{12}$ is trimethylammonium or —I$^+$—Ar, and the other is hydrogen. Preferably, one of $R^{11}$ and $R^{12}$ is trimethylammonium and the other is hydrogen. Most preferably, $R^{12}$ is nitro, trimethylammonium or —I$^+$—Ar, most especially preferably $R^{12}$ is nitro. $R^{13}$ is preferably C(=O)—O—R$^4$ wherein $R^4$ is ethyl, isopropyl or tert-butyl, and wherein $R^4$ is preferably ethyl.

BRIEF DESCRIPTION OF THE EXAMPLES

Comparative Example 1 describes the preparation of [$^{18}$F]flumazenil from a nitro precursor compound.

Example 2 describes the preparation of [$^{18}$F]flumazenil from a trimethylammonium precursor compound.

Example 3 describes the preparation of an iodonium salt precursor compound for [$^{18}$F]flumazenil.

Example 4 describes the preparation of ortho-[$^{18}$F]flumazenil from a nitro precursor compound.

Example 5 describes the preparation of ortho-[$^{18}$F]flumazenil tert-butyl ester from a nitro precursor compound.

Example 6 describes the preparation of ortho-[$^{18}$F]flumazenil isopropyl ester from a nitro precursor compound.

Example 7 describes a method for evaluation of the in vivo biodistribution of ortho-[$^{18}$F]flumazenil.

LIST OF ABBREVIATIONS USED IN THE EXAMPLES aq aqueous
CIP 2-Chloro-1,3-dimethylimidazolidium hexafluorophosphate
DCM dichloromethane
DIPEA N,N-Diisopropylethylamine
DMF dimethyl formamide
DMSO dimethyl sulfoxide
EOS end of synthesis
Et ethyl
g gram(s)
h hour(s)
HPLC high performance liquid chromatography
LCMS liquid chromatography mass spectrometry
MeCN acetonitrile
min minute(s)
mL milliliter(s)
mM millimolar
mmol millimole(s)
mol mole(s)
QMA quaternary methylammonium
Rf retention factor
rt room temperature
SPE solid phase extraction
TBA tetrabutylammonium
TEA triethanolamine
THF tetrahydrofuran
TLC thin layer chromatography
UV ultraviolet

EXAMPLES

Comparative Example 1

Preparation of [$^{18}$F]Flumazenil ([I$^{18}$F]FMZ) from Nitromazenil

Example 1(i)

Synthesis of 4-Methyl-7-nitro-3,4-dihydro-1H-benzo[e][1,4]diazepine-2,5-dione (1)

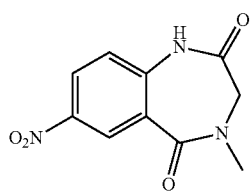

1

Commercially-available 5-Nitroisatoic anhydride (40 g, 0.192 mol) was dissolved in DMSO (50 mL) by stirring and heating the flask slowly to 140° C. Sarcosine (17.1 g, 0.192 mol) was slowly added in portions to the solution. Upon addition, at 140° C., the solution started bubbling (generation of CO$_2$). The mixture was left stirring for 2.5 h. The mixture was left to cool and slowly poured on ice cold water in a beaker. The solution was stirred with a glass rod and a yellow solid precipitated out. The solid was separated by filtration and washed several time with water, then dried in vacuum oven at 40° C. overnight. The yellow solid isolated was identified as the desired product 1 in a 78% yield.

$^1$H NMR (D$_6$-DMSO): δ 3.14 (3H, s, NCH$_3$), 3.97 (2H, s, NCH$_2$CO), 7.30 (1H, d, J=9 Hz, HNCCHCH), 8.33 (1H, dd, J=9 and 3 Hz, CHCHCNO$_2$CH), 8.33 (1H, d, J=3 Hz, OC—CCH), 11.05 (1H, s, NH).

Example 1(11)

Preparation of Nitromazenil (2)

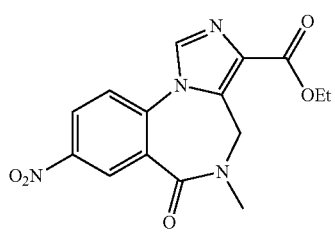

2

Potassium tert-butoxide (0.6 g, 5 mmol) was added to a solution of intermediate 1 (1 g, 4.3 mmol) in THF (10 mL) and DMF (2 mL) at 0° C. under nitrogen. After 30 min the reaction was cooled to 0° C., treated dropwise with diethyl chlorophosphate (0.7 mL, 5 mmol) and stirred for 30 min. Meanwhile to a stirred solution of ethyl isocyanoacetate (0.6 mL, 5 mmol) in THF (10 mL) under nitrogen at 0° C. was added potassium tert-butoxide (0.6 g, 5 mmol) and stirred for 15 min. This was then added slowly to the mixture of intermediate 1 at 0° C. This was stirred at 0° C. for 0.5 h then at room temperature for another 2 h. TLC (ethyl acetate) showed starting material (Rf 0.4) and a new spot (Rf 0.2) by UV and KMnO$_4$.

The reaction was quenched with acetic acid and left stirring overnight. The reaction mixture was poured into ice/water. This was extracted with ethyl acetate, and the organic layer was washed with water, brine, dried and concentrated to a thick dark dense oil. This was chromatographed on several times using the following conditions:

1) Companion, using DCMl/ethyl acetate (twice)
2) Companion using petrol/ethyl acetate (twice)

50 mg of the pure material 2 was obtained as a colourless solid (yield 4%)

$^1$H NMR (CDCl$_3$): δ 1.39 (3H, t, J=7 Hz, CH$_3$), 3.28 (3H, s, ArCONCH$_3$), 4.37 (2H, q, J=7 Hz, OCH$_2$), 4.40 (1H, br s, CH$_2$), 5.26 (1H, br s, CH$_2$), 7.60 (1H, d, J=8.9 Hz, ArCHCHCNO$_2$), 7.94 (1H, s, NCHN), 8.45 (1H, dd, J=8.9 and 2.8 Hz, ArCHCHCNO$_2$), 8.95 (1H, d, J=2.5 Hz, ArCHCNO$_2$).

Example 1(iii)

Radiofluorination of Nitromazenil (2) to Obtain [$^{18}$F]Flumazenil ([$^{18}$F]FMZ)

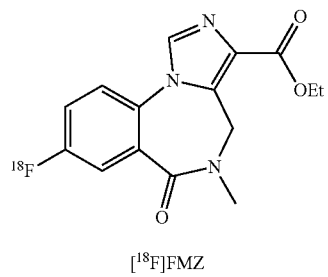 [SMILES: CCOC(=O)c1ncn2c1CN(C)C(=O)c1cc([18F])ccc1-2]

[$^{18}$F]FMZ $^{18}$F labeling was done on a TRACERlab automated synthesis module (GE Healthcare). [$^{18}$F] fluoride was trapped on a pre-conditioned QMA cartridge and then transferred to the reaction vessel using a solution of tetra-n-butylammonium bicarbonate in MeCN/water (MeCN 1400 μL, water 100 μL, TBA.HCO$_3$ 27 mg) from vial 1. The solution was dried at 100° C. for 10 minutes then 120° C. for 20 minutes using nitrogen plus vacuum flow and then cooled to 50° C.

To the dried [$^{18}$F]fluoride was added nitromazenil (18.8 mg) in DMF (1 mL) from vial 3. The reaction mixture was heated at 160° C. for 30 min then it was cooled to 50° C. The reaction mixture was diluted with 10 mM phosphoric acid (2.5 mL) from vial 5 and was transferred to the crude product tube.

The crude product was then transferred onto the preparative HPLC loop manually. Preparative HPLC gave a peak with retention time 17.5 minutes which was cut using into the TRACERlab round bottomed flask containing water (12 mL). The prepartative HPLC system was fitted with a liquid flow scintillation counter.

| HPLC Column | Phenomenex Luna C18(2) 250 × 10 mm 5μ |
|---|---|
| Solvent | A = 10 mM phosphoric acid, B = MeCN, 25% B isocratic |
| Flow rate | 4 mL/min |
| UV | 254 nm |
| Loop | 5 mL |
| Sensitivity | 2000K |

The mixture in the round bottom flask was trapped on a tC18 plus lite SPE cartridge (pre conditioned with 1 mL ethanol then 2 mL water). The SPE cartridge was washed with water (3 mL) and the crude product eluted into a P6 vial using EtOH (0.5 mL) and water (4.5 mL).

| Initial activity | 193.8 MBq | @11:14 |
| Activity of formulated product = | 14.8 MBq | @12:48 |
| 7.7% end of synthesis yield | | |

Example 2

Preparation of [$^{18}$F]Flumazenil ([$^{18}$F]FMZ) from a Trimethylammonium Precursor Compound

Example 2(i)

Synthesis of 4-methyl-7-Amino-3,4-dihydro-1H-benzo[e][1,4]diazepine-2,5-dione (3)

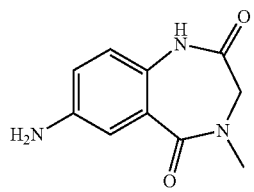

3

Intermediate 1 (3.48 g, 15 mmol, preparation described in Example 1) was suspended in a 120 mL of 1:1 solution of THF/Ethanol. The suspension was treated with nitrogen followed by vacuum, before adding Pd/C 10% (0.7 g), suspended in ethanol. The reaction vessel was then fitted onto the Parr hydrogenator and left under hydrogen pressure (20 psi) for about 3 hours with stirring. The excess hydrogen gas was removed using vacuum and then nitrogen was purged through the solution. The catalyst was filtered off using celite and the filtrate was evaporated to the minimum amount of ethanol. A white precipitate formed which was separated by filtration and dried under vacuum to afford 918 mg of desired material 3 in 30% yield.

$^{1}$H NMR (DMSO): δ 3.07 (3H, s, NCH$_3$), 3.74 (2H, s, NCH$_2$CO), 5.19 (2H, s, NH$_2$), 6.69 (1H, dd, J=8.6 and 2.5 Hz, ArCHCNH$_2$), 6.77 (1H, d, J=8.6 Hz, ArCHCNHCO), 6.90 (1H, d, J=2.5 Hz, COCCHCNH$_2$), 9.97 (1H, s, NH).

Example 2(iii)

Synthesis of 4-methyl-7-Dimethylamino-3,4-dihydro-1H-benzo[e][1,4]diazepine-2,5-dione (4)

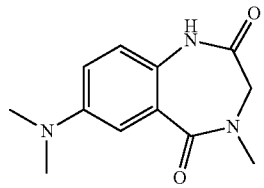

4

To a solution of intermediate 3 (3.0 g, 13 mmol) and 37% aq formaldehyde (21 mL, 0.26 mol) in acetonitrile at 0° C., NaBH$_3$CN (4.8 g, 77 mmol) was added portionwise. The reaction mixture was stirred at 0° C. for 2 h and then at room temperature for 1 h. Acetic acid (1.4 mL) was then added and the reaction mixture was stirred for another 2 h. The reaction mixture was poured into ethyl ether, washed with 2N KOH and the basic layer was extracted several times with ethyl acetate. The organic phases were collected and dried and solvents removed in vacuum to give an amorphous yellowish solid.

Notes: upon addition of acetic acid formation of gas was observed and the reaction was strongly exothermic.

The solid obtained was triturated with ethyl acetate, isolated by filtration and washed with diethyl ether to give a pale yellow fluffy solid. Proton NMR confirmed the material to be intermediate 4 (2.97 g, 98%).

$^{1}$H NMR (DMSO): δ 3.09 (3H, s, NCH$_3$), 3.77 (2H, s, NCH$_2$CO), 6.92-6.98 (3H, m, ArCHCN(CH$_3$)$_2$, ArCHCNHCO, COCCHCN(CH$_3$)$_2$), 10.09 (1H, s, NH).

Example 2(iii)

Synthesis of Trimethyl-(4-methyl-2,5-dioxo-2,3,4,5-tetrahydro-1H-benzo[e][1,4]diazepin-7-yl)-ammonium (5)

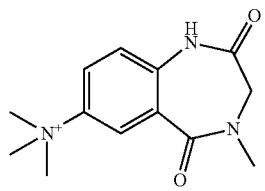

5

Intermediate 4 (2.97 g, 13 mmol) was dissolved in DCM (75 mL) and methyl triflate (1.67 mL, 15 mmol) was added at room temperature dropwise under nitrogen flow. Within 1 min a solid started to crash out of solution. After 10 min TLC analysis (ethyl acetate) showed that SM had disappeared. The reaction was therefore stopped. Diethyl ether (20 mL) was added and the solid was isolated by filtration as white sticky material. The reaction afforded intermediate 5 in quantitative yield.

$^{1}$H NMR (DMSO): δ 3.15 (3H, s, CONCH$_3$), 3.61 (9H, s, N$^+$(CH$_3$)$_3$), 3.91 (2H, s, NCH$_2$CO), 7.28 (1H, d, J=9.19 Hz, ArCHCNHCO), 8.10 (1H, dd, J=3.06 and 9.19 Hz, ArCHCN$^+$(CH$_3$)$_3$), 8.25 (1H, d, J=3.06 Hz, COCCHCN$^+$(CH$_3$)$_3$), 10.73 (1H, s, NH).

Example 2(iv)

Synthesis of the Trimethylammonium Precursor Compound (6)

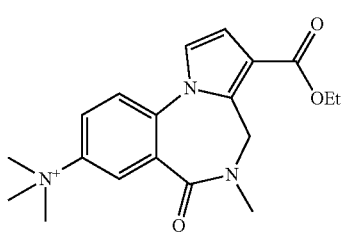

6

Sodium hydride (240 mg of a 60% dispersion in mineral oil, 6 mmol) was added to a solution of intermediate 5 (2 g, 5 mmol) in THF (15 mL) and DMF (10 mL) at room temperature under nitrogen. After 40 min the reaction was cooled to 0° C. and treated dropwise with diethyl chlorophosphate (1.08 mL, 7.5 mmol) and stirred for 30 min. Meanwhile to a stirred solution of ethyl isocyanoacetate (0.656 mL, 6 mmol) in DMF (6 mL) under nitrogen at 0° C. was added sodium hydride (280 mg of a 60% dispersion in mineral oil, 7 mmol) and stirred for 15 min. This was then added slowly to the mixture of intermediate 5 at 0° C. This was stirred at 0° C. for 0.5 h then room temperature for 30 mins. LCMS analysis of the crude after this time showed presence of desired mass. The reaction was quenched with acetic acid and worked up.

The reaction mixture was poured into ice/water. This was extracted with ethyl acetate, followed by DCM. LCMS analysis of the organics and the water suggested desired material present in the water layer. This was therefore taken to dryness (using rotary evaporation) and then the crude analysed by semiprep HPLC. The desired product 6 was isolated in 25% yield.

HPLC conditions: 5-95% methanol/water gradient over 30 mins; Luna 10☐ C18(2) 250×50 mm column.

$^1$H NMR (D$_2$O): δ 1.37 (3H, t, J=7.1 Hz, COOCH$_2$CH$_3$), 3.22 (3H, s, NCH$_3$), 3.73 (9H, s, N(CH$_3$)$_3$), 4.41 (2H, m, COOCH$_2$CH$_3$), 4. (1H, br d, J=15.3 Hz, NCH$_2$), 5.13 (1H, br d, J=15.3 Hz, NCH$_2$), 7.93 (1H, d, J=9.2 Hz, ArCHCNHCO), 8.25 (1H, dd, J=9.2 and 3.1 Hz, ArCHCN$^+$(CH$_3$)$_3$), 8.27 (1H, s, ArNCHN), 8.40 (1H, d, J=3.1 Hz, COCCHCN$^+$(CH$_3$)$_3$).

Example 2(v)

Radio Fluorination of Trimethylammonium Precursor Compound (6) to Obtain [$^{18}$F]Flumazenil ([$^{18}$F]FMZ)

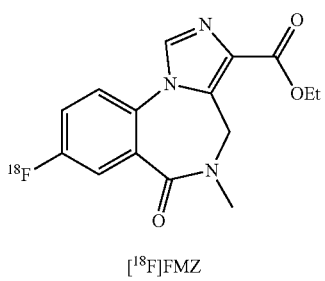 [SMILES: CCOC(=O)c1ncn2c1CN(C)C(=O)c1cc([18F])ccc1-2]

[$^{18}$F]FMZ

[$^{18}$F] fluoride was transferred to a Wheaton vial to which was added TBA.HCO$_3$ (400 µL). The solution was dried at 110° C. under a flow of N$_2$ (~0.5 L/min) for 30 min, then cooled to room temperature.

To the dried [$^{18}$F] fluoride was added the trimethylammonium precursor (31 mg) in DMSO (1 mL). The reaction mixture was heated at 130° C. for 25 min when it was cooled to room temperature. The reaction mixture was transferred from the Wheaton vial into a P6 vial. The Wheaton vial was rinsed with water (1 mL) and transferred to the P6 vial, an additional 3 mL off ammonium acetate (50 mM) was added. The reaction mixture was loaded onto preparative HPLC (Hichrom ACE C5 10×100 mm column; solvent A=50 mM Ammonium Acetate, solvent B=MeCN; 4 mL/min; UV 254 nm) for purification.

Analytical HPLC (Phenomenex Luna C18(2) 50×2 mm column; solvent A=50 mM Ammonium Acetate, solvent B=MeCN; 0.4 mL/min; UV 254 nm) confirmed that [$^{18}$F] flumazenil was obtained at 95% radiochemical purity. The end of synthesis yield of [$^{18}$F]flumazenil using this method was 6%.

Example 3

Preparation of an Iodonium Salt Precursor Compound for [$^{18}$F] Flumazenil ([$^{18}$F]FMZ)

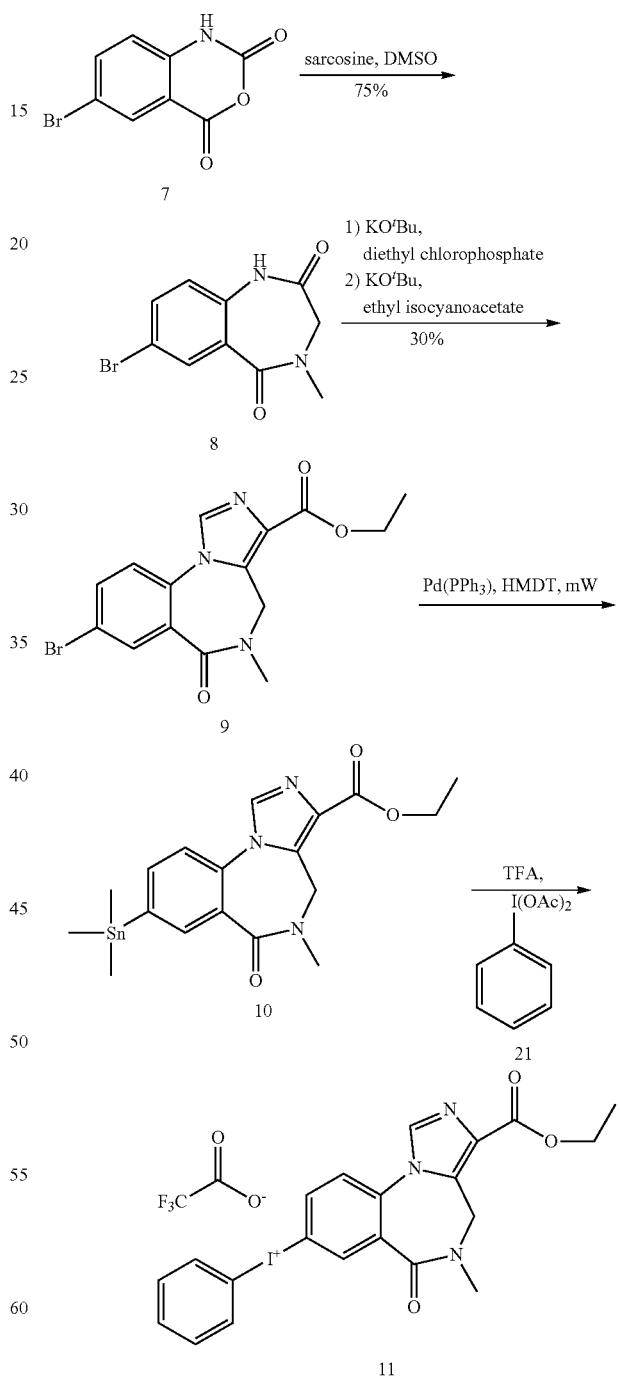

Commercially available 5-bromoisatoic anhydride (7) was heated in DMSO with sarcosine at 150° C. This afforded intermediate 8 in 75% yield. The annulation afforded intermediate 9 with a yield of 30% using the conditions illustrated in the reaction scheme. Intermediate 9 and hexamethylditin/Pd(PPh$_3$)$_4$ were heated in the microwave at 130° C. for 15 minutes to afford the stannane intermediate 10 in 35% yield. The iodonium conversion was obtained using a 1:5 ratio of intermediate 10 and (diacetoxyiodo)benzene, after 24 h at RT the reaction had gone to completion. The desired iodonium salt precursor compound 11 was obtained in 21% yield.

Example 4

Preparation of Ortho-[$^{18}$F]Flumazenil from Ortho-Nitromazenil

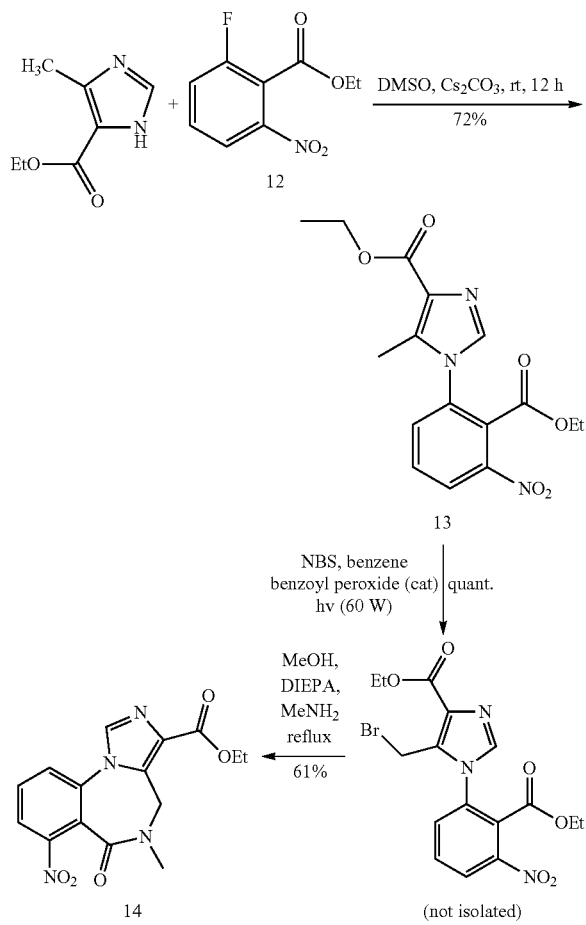

Example 4(i)

Preparation of 2-Fluoro-6-Nitro Benzoic Acid Ethyl Ester (12)

2-Fluoro-6-nitro benzoic acid (1.5 g, 8 mmol) was suspended in DCM (30 mL) under nitrogen flow at 0° C. Oxalyl chloride (1.5 g, 1.06 mL, 12 mmol) was slowly added and the reaction was left stirring overnight. The formation of the acyl chloride could be followed by TLC (ethyl acetate). The solvent was removed in vacuo and the residue was redissolved in DCM (20 mL). Ethanol (0.4 g, 0.5 mL, 8 mmol) was added at 0° C. with TEA (0.8 g, 1.1 mL, 8 mmol) and the reaction was left stirring at room temperature for 3 hours. After this time a small amount of mixture was analysed by $^1$H & $^{19}$F NMR to show quantitative formation of 12.

The reaction mixture was diluted with DCM (20 mL) and washed with water (2×50 mL). The organic layer was separated, dried over MgSO$_4$ and filtered. The solvent was removed to dryness to afford a brown oil, which gave white crystals of 12 (1.5 g, 88%) over time.

$^1$H NMR (300 MHz, CDCl$_3$): δ$_H$ 1.39 (3H, t, J=7.1 Hz, COOCH$_2$CH$_3$), 4.47 (2H, q, J=7.1 Hz, COOCH$_2$CH$_3$), 7.47 (1H, td, J=8.3 and 1.2 Hz, NO$_2$CCHCHCHCF), 7.59 (1H, td, J=8.3 and 5.2 Hz, NO$_2$CCHCHCHCF), 7.98 (1H, dt, J=8.3 and 0.9 Hz, NO$_2$CCHCHCHCF); $^{19}$F NMR (282 MHz, CDCl$_3$): □$_F$-112.4.

Example 4(ii)

Preparation of Intermediate 13

12 (3 g, 0.014 mol) and ethyl 4-methyl-5-imidazole-carboxylate (1.96 g, 0.013 mol) were dissolved in 30 mL of DMSO. Cesium carbonate (4.6 g, 0.014 mol) was added and the mixture was stirred at rt for 3 days.

Crude was analysed by LCMS using a 5-95% acetonitrile/water gradient over 3 min. This showed a new species with mass 348.03 in the positive.

TLC analysis (Ethyl acetate) showed a new spot with rf 0.4.

The reaction mixture was poured into ice water and then extracted with ethyl acetate (×1) followed by DCM (×3). The combined organics were concentrated and liquid loaded on silica column for flash chromatography (details on next page). The product 13 was isolated in 72% yield (3.5 g).

$^1$H NMR (CDCl$_3$): δ 1.19 (6H, t, J=7.05 Hz, COOOCH$_2$CH$_3$), 1.42 (3H, t, J=7.05 Hz, COOCH$_2$CH$_3$), 2.37 (3H, s, NCCH$_3$), 4.21 (2H, q, J=7.05 Hz, COOCH$_2$CH$_3$), 4.41 (2H, q, J=7.05 Hz, COOCH$_2$CH$_3$), 7.49 (1H, s, NCHN), 7.62 (1H, dd, J=7.97 Hz, CCHCHCHCNO$_2$), 7.77 (1H, t, J=7.97 & 8.27 Hz, CCHCHCHCNO$_2$), 8.37 (1H, dd, J=8.27 Hz, CCHCHCHCNO$_2$).

Example 4(iii)

Preparation of Ortho-Nitromazenil (14)

To a stirred solution of bromide (4.25 g, 0.010 mol) in 50 mL of methanol a solution of DIPEA (2.84 g, 3.8 mL, 0.022 mol) and methyl amine (6.5 mL of 2M solution in methanol, 0.013 mol) in methanol (50 mL) was slowly added. The reaction was refluxed overnight. TLC analysis using ethyl acetate showed quantitative conversion of the starting material 13 to two main new spots (rf 0.5 and 0.3). Crude was analysed by LCMS using a 5-95% acetonitrile/water gradient over 3 min. This showed a new species with mass 331.03 in the positive and two other major peaks. The solvent was removed to dryness and the crude was liquid loaded on column for flash chromatography using DCM/Ethyl acetate 1% methanol. LCMS of the 2 major combined fractions showed the desired material in a mixture with two other products.

Each fraction was submitted to a second purification using DCM/ethyl acetate. The product 14 was then re-crystallised from both fractions using ethanol. Desired material was isolated pure in 15% yield.

$^1$H NMR (CDCl$_3$) δ 1.43 (3H, s, CH$_3$), 3.20 (3H, s, NCH$_3$), 4.32-4.50 (2H, m, OCH$_2$), 4.54 (1H, d, J=16 Hz, NCH), 5.30 (1H, d, J=16 Hz, NCH'), 7.66 (1H, dd, J=8 Hz and 1 Hz, NCCH), 7.70 (1H, dd, J=8 and 8 Hz, CHCHCH), 7.94 (1H, dd, J=8 and 1 Hz, CHCNO$_2$), 7.97 (1H, s, NCHN).

Example 4(iv)

Radiofluorination of Ortho-Nitromazenil to Obtain Ortho-[$^{18}$F]Flumazenil Radiofluorination was done on a FASTlab automated synthesis module (GE Healthcare).

A cassette was assembled from component parts as follows. An 11 mm vial containing 20.5 mg K222, 140 μl K2CO3 (2.9 mg in water) & 1.06 ml MeCN, a second 11 mm vial containing 1.3 ml of precursor solution (6.5 mg precursor 14 in 1.3 ml of dry DMF), a 13 mm vial containing phosphoric acid (2.6 mL, 10 mM), a 13 mm vial containing saline (0.9%, 2.4 mL) and a 13 mm vial containing ethanol (4 mL) were inserted into the cassette. A pre-treated QMA cartridge was fitted, and a tC18+ cartridge.

The required operating sequence file was uploaded from the control PC into the internal memory of the FASTlab. The cassette was mounted on to the FASTlab synthesizer. The [$^{18}$F]fluoride vial was pierced using a needle connected to the line to the fluoride inlet on the FASTlab. A clean, empty product collection vial was connected which was pre filled with 0.9% saline (7 mL). The synthesis sequence was then commenced and the FASTlab hardware test step completed. The fluoride was trapped on the QMA cartridge and dried in the reaction vessel. The solution of precursor 14 was added and heated at 130° C. for 30 minutes. The reaction mixture was diluted with phosphoric acid (10 mM, 2.2 mL). Once the crude product had transferred to the HPLC loop, the HPLC run was started (see below for details of the preparative HPLC conditions).

| HPLC Column | Phenomenex Prodigy ODS-prep 250 × 10 mm 10μ |
|---|---|
| Solvent | A = 10 mM phosphoric acid, B = MeCN, 25% B isocratic |
| Flow rate | 4 mL/min |
| UV | 254 nm |
| Loop | 5 mL |
| Sensitivity | 200K |

Once the product had been injected onto the prep HPLC the cut (retention time 13.7 minutes) was performed manually for approximately minute into a vial containing ~13 ml water. The diluted cut was drawn back onto the FASTlab for reformulation on the tC18 plus cartridge. The amount of radioactivity in formulated product (in 1 mL ethanol and 9 mL saline) was measured in an ion chamber. A sample of product was sub dispensed and posted out of the hot cell for analysis.

| Initial activity | 21100 MBq | @12:00 |
|---|---|---|
| Activity of formulated product = 23% end of synthesis yield | 4880 MBq | @13:28 |

Radiochemcial purity was >99% two hours after the end of synthesis.

Total cold ligand measured by was 3 μg/10 mL volume. This is calculated using analytical HPLC UV peak area with the cold reference compound as calibrating standard.

This automated synthesis method produced radiolabeled material with approximately 1 μg of cold impurities total. This automated process also gave consistent yields over a range of starting radioactivity levels. The results from four consecutive syntheses are shown below.

| Non decay corrected EOS yield | Amount of formulated product (MBq) | Radiochemical purity | Amount of cold ligand μg | Amount of impurities μg |
|---|---|---|---|---|
| 18.22 | 72.7 | >99 | | |
| 23.13 | 4880 | >99 | | |
| 20.34 | 7220 | >99 | | |
| 21.59 | 38 | >99 | 0.6 | ~1.0 |

Example 5

Preparation of Ortho-[$^{18}$F]Flumazenil Tert-Butyl Ester from Ortho-Nitromazenil Tert-Butyl Ester (17)

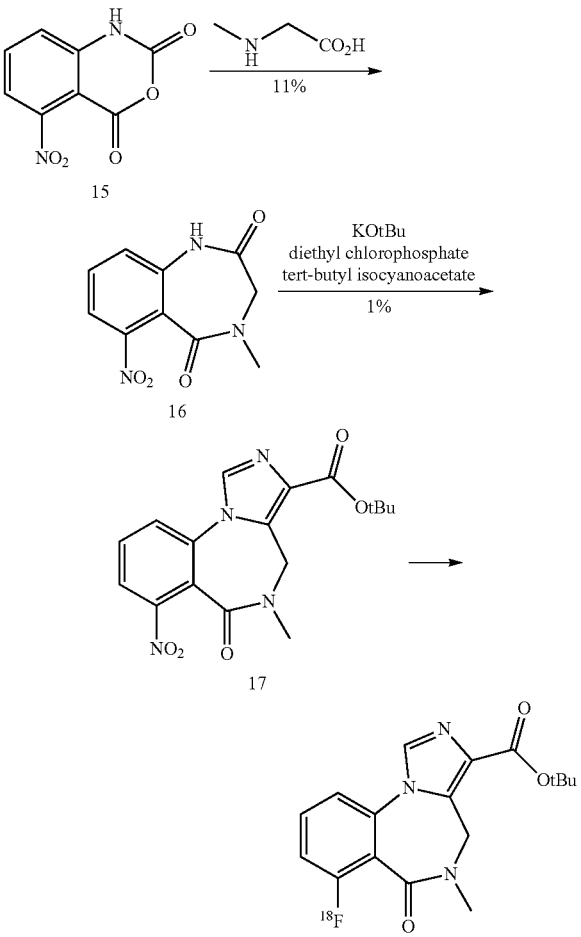

Example 5(i)

Preparation of Nitro Isatoic Acid (15)

2,6-Dinitrobenzoic acid (0.5 g, 2.36 mmol) in ethanol (5 mL) was heated to 80° C. Ammonium sulfide (40-48% in water) (0.36 mL, 2.36 mmol) was then added (the yellow solution became a bright orange suspension) the mixture was heated under reflux for 0.5 h. TLC (DCM 80%, MeOH 20%) showed a faint spot below the starting material. Ammonium sulfide (3.6 mL, 20.4 mmol) was added and the mixture became a darker orange. This mixture was then heated under reflux for 1 h after which time TLC indicated that the reaction had gone to completion. The solvents were removed under reduced pressure and then the residue washed with methanol.

The methanol solution was decanted off and evaporated to dryness to afford 2-nitro-6-amino benzoic acid as a orange solid. This was then purified using flash chromatography (DCM 90%/MeOH 10%->20% MeOH over 60CV, 12 g column) to afford the desired material (0.2 g, 46%).

$^1$H NMR (D$_6$-DMSO) δ 3.16 (2H, s, NH$_2$), 6.80 (1H, dd, J=8 and 1 Hz, H$_2$NCCH), 6.93 (1H, dd, J=8 and 1 Hz, CHCNO$_2$), 7.22 (1H, dd, J=8 and 8 Hz, CHCHCH).

2-nitro-6-amino benzoic acid (2.8 g, 15.4 mmol) was dissolved in dioxane (20 mL).

Triphosgene (1.52 g, 5.1 mmol) was added. The mixture was then heated under reflux for 1 h. The mixture was then allowed to cool. The precipitate was then collected by filtration to give the isatoic anhydride in quantitative yield.

$^1$H NMR (D$_6$-DMSO) δ 7.33 (1H, dd, J=8 and 1 Hz, ArCH), 7.59 (1H, dd, J=8 and 1 Hz, ArCH), 7.89 (1H, dd, J=8 Hz, ArCH), 12.2 (1H, br s, NH).

Example 5(ii)

Preparation of 4-Methyl-6-nitro-3,4-dihydro-1H-benzo[e][1,4]diazepine-2,5-dione (16)

Nitro isatoic acid (15) (3.5 g, 16.8 mmol) and sarcosine (1.50 g, 16.8 mmol) was dissolved in DMSO (8 mL). The mixture was then placed in a preheated heating mantle at 150° C. The mixture was then heated at this temperature for ca. 30 minutes; after which time the reaction mixture was poured into water (50 mL). The resulting brown precipitate was collected by filtration and triturated with ethyl acetate to afford a pale brown powder (0.9 g, 11%).

$^1$H NMR (300 MHz, DMSO-d$_6$): δ$_H$ 3.08 (3H, s, NCH$_3$), 4.16 (2H, br s, CH$_2$), 7.39 (1H, dd, J=8.0 and 2.0 Hz, HNCCH), 7.66 (1H, dd, J=8.0 and 8.0 Hz, CHCHCH), 7.72 (1H, dd, J=8.0 and 2.0 Hz, CHCNO$_2$), and 10.80 (1H, brs, NH); $^{13}$C NMR (300 MHz, DMSO-d$_6$): δ$_C$ 34.9 (NCH$_3$), 51.8 (NCH$_2$), 119.9 (CHCHCNH), 121.0 (C=CO), 125.1 (CHCHCNO$_2$), 138.3 (CNH), 151.0 (C—NO$_2$), 163.2 (C=O), and 169.7 (C=O).

Example 5(iii)

Preparation of Ortho-Nitromazenil Tert-Butyl Ester (17)

Potassium tert-butoxide (0.37 g, 3.27 mmol) was added to intermediate 16 (0.7 g, 2.98 mmol) in THF (56 mL) at 0° C. The mixture was then stirred at 0° C. for 20 min (during which time a bright yellow precipitate was observed) and then cooled to −35° C. Diethyl chlorophosphate (0.67 g, 3.88 mmol, 0.56 mL) was added slowly. The reaction was stirred at 0° C. for 30 min during which time mixture became slightly more yellow in colour. The reaction flask was cooled to −35° C. and solution of tert-butyl isocyanoacetate (0.46 g, 3.26 mmol, 0.48 mL) was added followed by potassium tert-butoxide (0.37 g, 3.27 mmol). The suspension was then left to stir at room temperature overnight. The reaction was quenched with aq NaHCO$_3$ (50 mL) and extracted with EtOAc (3×50 mL). The combined organic layers were dried over MgSO$_4$, concentrated to afford brown oil. The crude material was purified by silica gel chromatography eluting with ethyl acetate (A): methanol (B) (0-1% B, 100 g, 40 mL/min). 17 was obtained as a pale yellow solid (9 mg, 1%).

$^1$H NMR (300 MHz, CDCl$_3$): δ$_H$ 1.64 (9H, s, C(CH$_3$)$_3$), 3.19 (3H, s, NCH$_3$), 4.52 (1H, d, J=15.0 Hz, CONCH$_3$CH$_a$H$_b$), 5.45 (1H, d, J=15 Hz, CONCH$_3$CH$_a$H$_b$), 7.64 (1H, dd, J=9.0 and 3.0 Hz, NCCHCH), 7.73 (1H, dd, J=9.0 and 9.0 Hz, NCCHCH), 7.93 (1H, dd, J=9.0 and 3.0 Hz, O$_2$NCCHCHCH), and 7.94 (1H, s, NCHN).

Example 5(iv)

Radiofluorination of Ortho-Nitromazenil Tert-Butyl Ester (17) to Obtain Ortho-[$^{18}$F]Flumazenil Tert-Butyl Ester Radiofluorination was done on a TRACERlab automated synthesis module (GE Healthcare). The [18F] fluoride was trapped on a pre-condtioned QMA cartridge and then transferred to the reaction vessel using a solution of 4,7,13,16,21,24-Hexaoxa-1,10-diazabicyclo[8.8.8]hexacosane (KRYPTOFIX 222™) (11 mg) in MeCN (2000 μL) and K2CO3 (in 80 μL water, 1.7 mg) from vial 1. The solution was dried at 100° C. for 10 minutes then 120° C. for 20 minutes using nitrogen plus vacuum flow and then cooled to 50° C.

To the dried [$^{18}$F]fluoride was added ortho-nitromazenil tert-butyl ester (17, 5 mg) in DMF (1 mL) from vial 3. The reaction mixture was heated at 130° C. for 30 min then it was cooled to 50° C. The reaction mixture was diluted with 10 mM phosphoric acid (2.5 mL) from vial 5 and was transferred to the crude product tube.

The crude product was then transferred onto the preparative HPLC loop manually. Preparative HPLC gave a peak with retention time 13.5 minutes which was cut into the TRACERlab round bottomed flask containing water (12 mL). The preparative HPLC system was fitted with a liquid flow scintillation counter.

| | |
|---|---|
| HPLC Column | Phenomenex Prodigy ODS-prep 250 × 10 mm 10μ |
| Solvent | A = 10 mM phosphoric acid, B = MeCN, 30% B isocratic |
| Flow rate | 4 mL/min |
| UV | 254 nm |
| Loop | 5 mL |
| Sensitivity | 2000K |

The mixture in the round bottom flask was trapped on a C18 liter SPE (pre conditioned with 1 mL ethanol then 2 mL water). The SPE was washed with water (3 mL) and the crude product eluted into a P6 vial using EtOH (0.5 mL) and phosphate buffered saline (4.5 mL). The product was further diluted using phosphate buffered saline to give a final volume of 10 mL.

| | | |
|---|---|---|
| Initial activity | 828 MBq | @9:59 |
| Activity of formulated product = 14.6% end of synthesis yield | 121 MBq | @11:51 |

Radiochemcial purity was >99% two hours after the end of synthesis.

Total cold ligand measured by was 6 μg/10 mL volume (calculated using analytical HPLC UV peak area with the cold reference compound as calibrating standard).

Example 6

Radiofluorination of Ortho-Nitromazenil Isopropyl Ester (18) to Obtain Ortho-[$^{18}$F]Flumazenil Isopropyl Ester

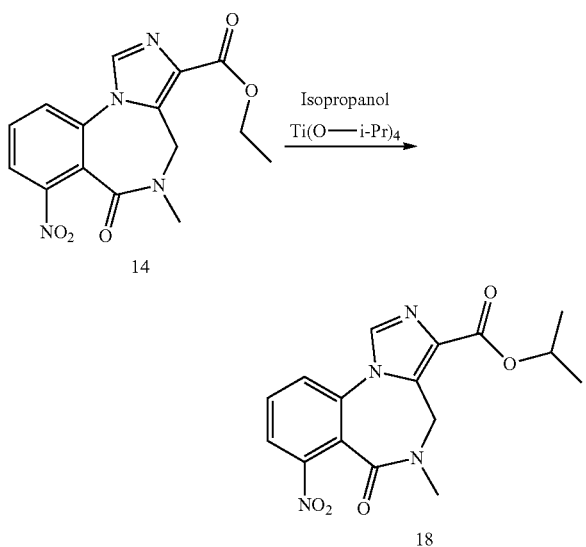

Example 6(i)

Preparation of Ortho-Nitromazenil Isopropyl Ester (18)

14 (preparation described in Example 4(iii); 20 mg, 0.06 mmol) was dissolved in 2 mL of isopropanol in a microwave vessel and 50 μl of Titanium (IV) isopropoxide were added. Microwave conditions: Temperature: 85° C.; Time: 60 mins. LCMS confirmed quantitative conversion of the starting material to the desired product. This was also confirmed by TLC using ethyl acetate. The excess isopropanol was removed to dryness and the crude mixture was liquid loaded on column for flash chromatography using petrol and ethyl acetate as eluent. The material was purified again using DCM/Methanol. 18 (15 mg) was obtained pure (73%).

$^1$H NMR (CDCl$_3$) δ 1.43 (3H, d, J=6.1 Hz, C$\underline{H}_3$), 1.45 (3H, d, J=6.1 Hz, C$\underline{H}_3$), 3.20 (3H, s, NC$\underline{H}_3$), 4.53 (1H, d, J=16 Hz, C$\underline{H}$), 5.28 (1H, d, J=16 Hz, C$\underline{H}$'), 5.33 (1H, m, COOCH (CH$_3$)$_2$), 7.66 (1H, dd, J=0.92, 8.27 Hz, C$\underline{H}$CHCHCNO$_2$), 7.75 (1H, t, J=8.3 Hz, CHC$\underline{H}$CHCNO$_2$), 7.94 (1H, dd, J=0.92, 8.27 Hz, CHCHC$\underline{H}$CNO$_2$), 7.97 (1H, s, NC$\underline{H}$N).

Example 6(ii)

Radiofluoriantion of Ortho-Nitromazenil Isopropyl Ester (18) to Obtain Ortho-[$^{18}$F]Flumazenil Isopropyl Ester Radiofluorination was done on a TRACERlab automated synthesis module (GE Healthcare). The [$^{18}$F] fluoride was trapped on a pre-condtioned QMA cartridge and then transferred to the reaction vessel using a solution of 4,7,13,16,21,24-Hexaoxa-1,10-diazabicyclo[8.8.8]hexacosane (KRYPTOFIX 222™) (11 mg) in MeCN (2000 μL) and K$_2$CO$_3$ (in 80 μL water, 1.7 mg) from vial 1. The solution was dried at 100° C. for 10 minutes then 120° C. for 20 minutes using nitrogen plus vacuum flow and then cooled to 50° C.

To the dried [$^{18}$F]fluoride was added ortho-nitromazenil tert-butyl ester (2.5 mg) in DMF (1 mL) from vial 3. The reaction mixture was heated at 130° C. for 30 min then it was cooled to 50° C. The reaction mixture was diluted with 10 mM phosphoric acid (2.5 mL) from vial 5 and was transferred to the crude product tube.

The crude product was then transferred onto the preparative HPLC loop manually. Preparative HPLC gave a peak with retention time 23 minutes which was cut into the TRACERlab round bottomed flask containing water (15 mL). The prepartative HPLC system was fitted with a liquid flow scintillation counter.

| HPLC Column | Phenomenex Prodigy ODS-prep 250 × 10 mm 10μ |
|---|---|
| Solvent | A = 10 mM phosphoric acid, B = MeCN, 25% B isocratic |
| Flow rate | 4 mL/min |
| UV | 254 nm |
| Loop | 5 mL |
| Sensitivity | 2000K |

The mixture in the round bottom flask was trapped on a C18 liter SPE (pre conditioned with 1 mL ethanol then 2 mL water). The SPE was washed with water (3 mL) and the crude product eluted into a P6 vial using EtOH (0.8 mL) and phosphate buffered saline (7.2 mL).

| Initial activity | 800 MBq | @10:51 |
|---|---|---|
| Activity of formulated product = 14.2% end of synthesis yield | 114 MBq | @12:56 |

Radiochemcial purity was >99% three hours after the end of synthesis.

Total cold ligand measured by was 2.4 μg/8 mL volume (calculated using analytical HPLC UV peak area with the cold reference compound as calibrating standard). Total cold impurities were approximately 2 μg.

Example 7

In Vivo Biodistribution of Ortho-[$^{18}$F]-Flumazenil

Adult male Sprague-Dawley rats (body weight 202±37 g; mean±SD) were injected with between 1 and 5 MBq of ortho-[$^{18}$F]-flumazenil via a lateral tail vein. All animals were conscious, but lightly restrained during injection and subsequently housed in short-term metabolism cages. At the appropriate time point; 30 seconds, 2, 10, 30 and 60 minutes post-injection (pi) (n=3 per time point), the animals were sacrificed by cervical dislocation. The brain and peripheral tissues or fluids were sampled post-mortem. Radioactivity in the brain samples was measured using a Wallac gamma counter. Once assayed, the brain samples, along with the remaining organ or tissue samples were assayed using a twin-crystal gamma-counter system (BASIL), with automatic correction for radioactive decay. The table below shows the data obtained in the brain regions. Data is expressed as mean (±SD), and all are n=3. Data indicated by an asterisk (*) is % id/g.

| Brain Region (% id/g) | Distribution of ortho-[$^{18}$F]-flumazenil Time Post-Injection [minutes (standard deviation)] | | | | |
|---|---|---|---|---|---|
| | 0.5 | 2 | 10 | 30 | 60 |
| Striatum | 0.90 (0.02) | 0.83 (0.22) | 0.68 (0.08) | 0.15 (0.02) | 0.06 (0.03) |
| Cerebellum | 0.99 (0.08) | 1.01 (0.28) | 0.96 (0.07) | 0.38 (0.08) | 0.11 (0.02) |
| Hippocampus | 0.81 (0.04) | 0.78 (0.25) | 0.91 (0.06) | 0.48 (0.10) | 0.17 (0.01) |
| Pre-frontal cortex | 1.12 0.03) | 1.14 (0.28) | 1.39 (0.06) | 0.76 (0.20) | 0.29 (0.04) |
| Thalamus | 1.03 (0.18) | 0.85 (0.29) | 0.94 (0.15) | 0.33 (0.07) | 0.08 0.02) |
| Pituitary gland | 0.98 (0.14) | 1.12 (0.31) | 0.46 (0.08) | 0.15 (0.09) | 0.02 (0.01) |
| Pons/Medulla | 0.79 (0.03) | 0.79 (0.22) | 0.59 (0.05) | 0.21 (0.15) | 0.24 (0.38) |
| Pre-frontal cortex: thalmus | 1.11 | 1.37 | 1.50 | 2.28 | 3.96 |

Initial uptake of radioactivity in the brain was 1.4±0.8% id after 30 seconds pi, peaking at 1.8±0.5% id at 2 minutes pi. After 2 minutes pi there was a steady decrease in radioactivity levels, with 0.9±0.2% id after 30 minutes pi falling to 0.3±0.1% id by 60 minutes pi.

The region with the highest levels of radioactivity at the early time points was the pre-frontal cortex (1.39±0.06% id at 10 minutes pi). There was good differentiation between the GABA-rich and GABA-poor regions to 30 min pi.

What is claimed is:

1. A method to obtain a compound of Formula I:

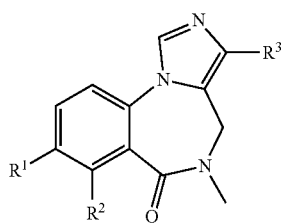

(I)

wherein:
$R^1$ is hydrogen and $R^2$ is $^{18}$F; and,
$R^3$ is a $C_{3-5}$ heterocycle; or, $R^3$ is C(=O)—O—$R^4$ wherein $R^4$ is hydrogen, or a straight- or branched-chain $C_{1-4}$ alkyl;
wherein said method comprises:
(i) providing a precursor compound of Formula Ia:

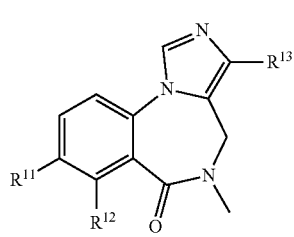

(Ia)

wherein:
$R^{11}$ is hydrogen and $R^{12}$ is a leaving group selected from nitro, tri-$C_{1-3}$ alkyl ammonium or —I$^+$—Ar, wherein Ar is phenyl substituted with one or more R* groups, wherein R* is selected from hydrogen, nitro, cyano, halogen, $C_{2-10}$ carboxyalkyl, $C_{1-10}$ alkyl, $C_{2-10}$ alkoxyalkyl, $C_{1-10}$ hydroxyalkyl, $C_{1-10}$ aminoalkyl, $C_{1-10}$ haloalkyl, $C_{6-14}$ aryl, $C_{3-12}$ heteroaryl, $C_{3-20}$ alkylaryl, $C_{2-10}$ alkenyl, and $C_{2-10}$ alkynyl; and,
$R^{13}$ is as defined for $R^3$ of Formula I; and,
(ii) reacting said precursor compound with a suitable source of [$^{18}$F]Fluoride.

2. The method as defined in claim 1 wherein $R^{12}$ is trimethyl ammonium.

3. The method as defined in claim 1 wherein $R^{12}$ is I$^+$—Ar.

4. The method as defined in claim 1 wherein $R^{12}$ is nitro.

5. The method as defined in claim 1 wherein $R^3$ and $R^{13}$ are independently C(=O)—O—$R^4$ wherein $R^4$ is a straight- or branched-chain $C_{1-4}$ alkyl.

6. The method as defined in claim 5 wherein $R^4$ is ethyl, isopropyl or tert-butyl.

7. The method as defined in claim 1 wherein said suitable source of [$^{18}$F]Fluoride is selected from [$^{18}$F] potassium fluoride and [$^{18}$F] caesium fluoride.

8. The method as defined in claim 7 wherein said suitable source of [$^{18}$F]Fluoride is [$^{18}$F] potassium fluoride and 4,7,13,16,21,24-Hexaoxa-1,10-diazabicyclo[8.8.8]hexacosane is used to activate the fluoride ion.

9. The method as defined in claim 1, which further comprises:
(iii) removal of excess [$^{18}$F]Fluoride; and/or,
(iv) removal of any protecting groups and/or,
(v) removal of organic solvent.

10. The method as defined in claim 1 wherein said method is automated.

11. A compound of Formula I

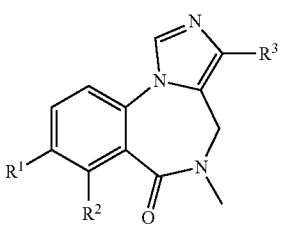

(I)

wherein $R^1$ is hydrogen, $R^2$ is $^{18}$F, $R^3$ is —C(=O)—O—$R^4$, wherein $R^4$ is ethyl, isopropyl or tert-butyl.

* * * * *